United States Patent [19]
Jorge

[11] Patent Number: 6,043,400
[45] Date of Patent: Mar. 28, 2000

[54] CHLOROHYDRIN PROCESS

[75] Inventor: Edward M. Jorge, Midland, Mich.

[73] Assignee: The Dow Chemical Company, Midland, Mich.

[21] Appl. No.: 08/765,755

[22] Filed: Dec. 30, 1996

Related U.S. Application Data

[63] Continuation of application No. 08/269,469, Jun. 30, 1994, abandoned.

[51] Int. Cl.[7] .................................................. C07C 29/00
[52] U.S. Cl. ........................... 568/850; 568/812; 568/844; 568/847
[58] Field of Search .................................... 568/840, 844, 568/850, 891, 812, 847

[56] References Cited

U.S. PATENT DOCUMENTS 4,410,714  10/1983  Apanel .

FOREIGN PATENT DOCUMENTS 45-4042  of 1970  Japan .

*Primary Examiner*—Michael L. Shippen
*Attorney, Agent, or Firm*—John B. Treangen

[57] ABSTRACT

This invention is a process for preparing chlorohydrins by reacting a chlorinating species, such as hypochlorous acid, with at least one unsaturated organic compound, such as propylene or butylene, at a pH of greater than 6.0. The chlorinating species is formed in a first step by reacting a source of chlorine, such as $Cl_2$ gas, with an aqueous pH adjusting source, such as aqueous NaOH.

8 Claims, No Drawings

CHLOROHYDRIN PROCESS

CROSS-REFERENCE TO RELATED APPLICATIONS

This Application is a continuation of U.S. patent application Ser. No. 08/269,469 filed Jun. 30, 1994, now abandoned and is a 371 of International Patent Application No. PCT/US95/06584, filed May 24, 1995, and published as WO 96/00709 on Jan. 11, 1996.

BACKGROUND AND DESCRIPTION OF THE INVENTION

The present invention relates to the production of chlorohydrins.

Chlorohydrins are useful as intermediates in producing various compounds. For example, propylene chlorohydrin and butylene chlorohydrin are used in producing propylene oxide and butylene oxide, respectively.

Various processes are known for the production of chlorohydrins. For example, olefin chlorohydrins are typically prepared by reacting an olefin with chlorine in the presence of water. This process is believed to occur by means of an intermediate cyclic chloronium ion which reacts with the water to form an olefin chlorohydrin. However, the process also concurrently forms undesirable dichloride byproducts when aqueous chloride ions react with the cyclic chloronium ions. Significant yield losses are typically suffered and the byproducts must be separated from the desired olefin chlorohydrin, an operation that adds to the cost of making the chlorohydrin.

One reference, SU-A-247281 (Choporov YA P, 1976), discloses a process for producing chlorohydrins by reacting olefins with hypochlorous acid, wherein the process requires preliminarily acidifying the olefin with gaseous hydrochloric acid and carrying out the process at a pH of between 4 to 7, and preferably between 5 to 6. The reference reports that by this method of acidifying the olefin, the reaction is accelerated, the concentration of the product in the solution is increased and so are the yields.

A second reference, JP-A-05025071 (Tokuyama Soda KK, 1976), discloses preparation of chlorohydrins by, first, preparing hypochlorous acid by reacting chlorine and water in the presence of alkali(ne earth) metal hydroxides (maintaining a pH below 7.0), then, reacting the hypochlorous acid mixture with a vinyl group-containing compound. This reference reports that when such pH of the hypochlorous acid mixture is below 7.0, upon reaction with the vinyl group, the concentration and yield of the resulting chlorohydrin product are increased.

Various other methods of forming chlorohydrins are also well known such as reacting olefins with t-butyl hypochlorite or hypochlorous acid substantially free of chloride ions. However, these methods typically either result in the production of numerous byproducts or require various, costly processing steps or long reaction times, thus hindering the commercial viability of the methods. For these reasons, there remains a need for a process for producing chlorohydrin that is effective and results in high yields of the desired product.

The process of this invention requires a first step of contacting a chlorine source with an aqueous pH adjusting source under conditions sufficient to form a chlorinating species. In a second step, the chlorinating species is contacted with at least one unsaturated organic compound under conditions sufficient to form the chlorohydrin. During this process the aqueous pH adjusting source must be sufficient to maintain a pH of greater than 6.0 throughout the second step (the "chlorohydrin forming step"). This process results in a reduction of byproduct formation and a production of higher yields of the desired chlorohydrins.

The chlorine source may be any source of chlorine that is capable of forming the chlorinating species upon reaction with the pH adjusting source. Examples of such chlorine sources are chlorine ($Cl_2$), hypochlorous acid (HOCl), chlorine monoxide ($Cl_2O$), or a hypochlorite (—OCl) of an alkali metal or alkaline earth metal. The chlorine source is preferably $Cl_2$, more preferably, $Cl_2$ gas.

The pH adjusting source may be any composition capable of maintaining a pH of greater than 6.0, preferably greater than 7.0, and most preferably greater than 7.5 throughout the chlorohydrin forming step. The pH is preferably maintained at less than 10.0 and more preferably less than 9.5. When the pH is greater than 6.0, conditions are favored in the chlorohydrin forming step for the reaction of the chloronium ion intermediate with water or hydroxide ion, thus increasing yield of chlorohydrin. It is believed that above a pH of about 10.0 reaction kinetics may begin to slow and formation of byproducts such as glycol may also increase.

A preferable pH adjusting source is an aqueous mixture containing at least one type of ion selected from the group consisting of hydroxide, oxide, hypohalite, bicarbonate, and carbonate. The aqueous mixture is preferably a solution or slurry that contains at least one type of metal ion selected from the group consisting of ions of alkaline earth metals and alkali metals. For example, preferable aqueous pH adjusting sources comprise aqueous mixtures containing compounds such as calcium hydroxide ($Ca(OH)_2$), sodium hydroxide (NaOH), magnesium hydroxide ($Mg(OH)_2$), potassium hydroxide (KOH), sodium carbonate ($Na_2CO_3$), sodium bicarbonate ($NaHCO_3$), calcium carbonate ($CaCO_3$), and calcium oxide (CaO). Preferable hypohalites include alkali metal hypochlorites (e.g. sodium hypochlorite (NaOCl)) and alkaline earth metal hypochlorites (e.g. calcium hypochlorite ($Ca(OCl)_2$). Irrespective of which chlorine source and pH adjusting source are used, concentration of the pH adjusting source must be sufficient to maintain a pH of greater than 6.0 in the chlorohydrin forming step of this invention. For example, a preferable concentration of pH adjusting source in water ranges from 0.1 normal (N) to 1.5 N and more preferably from 0.2 to 0.5 N. Skilled artisans will recognize that some pH adjusting sources may have low solubilities in water, but for purposes of this invention the preferred concentrations reflect concentrations as if the pH adjusting source were completely soluble in water.

One or more surfactants may be included in the process of this invention. Although not critical, the use of a surfactant may be desirable, particularly in those instances where the unsaturated organic compound is highly insoluble in water. The type of surfactant used is not critical. Thus, anionic, nonionic, cationic, and amphoteric surfactants may be employed. Examples include: anionic surfactants such as alkylbenzenesulfonates, alkanesufonates, x-olefinsulfonates; cationic surfactants such as quaternary ammonium compounds; nonionic surfactants such as alkyl poly (ethylene glycol) ethers, alkylphenol poly(ethylene glycol) ethers, fatty acid alkanolamides, and fatty alcohol polyglycol ethers; amphoteric surfactants such as alkylbetaines and alkylsulfobetaines.

The optimum temperature, pressure, and time of contact for the chlorine source and the pH adjusting source depend upon the reactants and apparatus used. These variables may be determined by skilled artisans without undue experimentation. For example, when the chlorine source is $Cl_2$ gas and the pH adjusting source is aqueous NaOH, a period of time sufficient to complete the reaction and form the chlorinating species is usually less than ten seconds in a reactor which is at ambient temperature (about 23° C.) and pressure (about 101 kPa). Typically, formation of the chlorinating species may be conducted at any temperature between 0° C. and 100° C., preferably 0° C. to 70° C., and most preferably 10° C. to 30° C. Any pressure between 0 psig (101 kPa) and 100 psig (791 kPa) is typically appropriate. It is generally most convenient to conduct the reaction at ambient temperature and pressure.

The contact may occur in a continuous or semi-continuous reactor. In a continuous reactor, such as a continuous tubular reactor, reactants are introduced and products withdrawn simultaneously. In contrast, an example of a semi-continuous reactor would be a reactor having a specific amount of pH adjusting source already placed in the reactor, then having a continuous feed of the chlorine source fed to the reactor, producing products which accumulate in the reactor. It is preferred that the contact occur in the presence of mixing and most preferred that It be conducted in a backmix reactor. A backmix reactor is defined as a reactor in which reaction products are intimately mixed with feed materials, resulting in uniform product and reactant concentrations throughout the reaction vessel. An example of a continuous reactor of this type is a continuous-flow stirred tank reactor (CSTR).

The chlorinating species formed from contacting the chlorine source with the pH adjusting source in this first step of the invention may comprise at least one compound selected from the group consisting of hypochlorous acid, alkali metal hypohalites, and alkaline earth metal hypohalites.

The second step of the invention is the chlorohydrin forming step. This step comprises contacting the chlorinating species with at least one unsaturated organic compound containing from 2 to 10 carbon atoms, preferably 2 to 8 carbons, and more preferably 2 to 6 carbons. The unsaturated organic compound may be selected from the group consisting of substituted and unsubstituted olefins and cyclic olefins. The substituted olefins may have substituents selected from the group consisting of an alkyl radical, a phenyl radical and an alkylphenyl radical (i.e. tolyl, xylyl or ethylphenyl). Each of these radicals may also be unsubstituted or substituted. When substituted, the substituents preferably comprise halides, hydroxides, or inert substituents. By "inert substituents" it is meant that the substituents do not interfere with the process of this invention. Any suitable unsaturated compound containing from 2 to 10 carbon atoms and meeting the criteria specified above can be used in the process of the invention to prepare the corresponding chlorohydrin. Such unsaturated organic compounds include, but are not limited to, ethylene, propylene, butylene, hexene, cyclohexene, cyclopentene, cyclooctene, and mixtures thereof. Examples of substituted olefins include allyl alcohol, allyl chloride, styrene, 4-bromo-1-butene, 3-chloro-1-butene, 3-chloro-2-methylpropene, 1-hexene-3-ol, 3-butene-2-ol, 3-pentene-2-ol, 1-octene-3-ol, and mixtures thereof.

For optimum results, the organic compound is typically added in an amount sufficient to provide a molar ratio of organic compound to chlorinating species of greater than 0.8. A skilled artisan is fully capable of employing various known methods of recycling unreacted compounds when the compounds are supplied in excess of that needed for the reaction. However, without recycle, the molar ratio is preferably less than about 1.20. More preferably, without recycle, an about 1 to 1 molar ratio of organic compound to chlorinating species is provided.

As with the first step of this invention, the chlorohydrin forming step is also conducted with mixing and at a temperature between 0 to 100° C. and pressure between ambient to 100 psig (791 kPa). Preferably, the temperature is from 20° C. to 80° C., more preferably from 40° C. to 60° C.

The organic compound may be contacted with the chlorinating species by any method sufficient to form the chlorohydrin. This is typically accomplished by introducing the organic compound and the chlorinating species into a reactor in a manner so as to allow maximum uniformity of all of the reactor's contents. A backmix reactor, as defined previously, is a preferable reactor for this step. For example, the chlorohydrin may be formed by contacting the organic compound with the chlorinating species in a CSTR. Product recovery may then be achieved by any convenient means such as extraction or distillation.

ILLUSTRATIVE EMBODIMENTS OF THE INVENTION

The invention will be further clarified by a consideration of the following examples, which are intended to be purely exemplary of the use of the invention.

In Examples 1–5 the chlorine source was $Cl_2$ gas (99.5% pure), and it was supplied to and mixed in a continuous tubular reactor (0.5 cm in diameter and 61 cm long) with the pH adjusting source, aqueous NaOH ("caustic"), forming a product solution containing a mixture of HOCl and NaOCl chlorinating species. The average residence time in the continuous tubular reactor was less than 10 seconds. The product solution containing the chlorinating species was then continuously supplied to a water jacketed CSTR reactor having a volume of 3.5 liters. The CSTR reactor was baffled and mixing was provided by an agitator having twin, 5-bladed, flat turbine impellers positioned one above the other on an agitator shaft. The CSTR reactor, agitator, and baffles were made of clear glass and the reactor was maintained at ambient pressure and a pH of greater than 6.0. Butylene (99% pure) was used as the olefin and was supplied to and entered the reactor below the bottom impeller through a glass-fritted sparger (10–50 micrometer pore size). The butylene was sparged into the reactor at a rate sufficient to maintain a slight molar excess. After steady-state conditions had been reached, organic material in the CSTR output was analyzed by gas chromatography for the desirable compounds which included 1,2 (and 2,1)-butylene chlorohydrin (BCH), and 1,2-butylene oxide (BO), and the undesirable "byproducts" which included 1,2-dichlorobutane, 1,2-butylene glycol, chloro-butylene chlorohydrin, 1,3butylene chlorhydrin, and bis-clorobutyl ether. Essentially complete conversion of the chlorinating species occurred in all of the examples.

EXAMPLE 1

A 28° C. aqueous stream containing 1.12 wt % caustic (based on weight of NaOH in the NaOH/water mixture) was pumped at 161 grams/minute (g/min.) into the continuous tubular reactor and $Cl_2$ was added at a rate of 2.8 g/min. The resulting chlorinating species containing solution was then added to the CSTR. The butylene was added to the CSTR at a rate of 2.2 g/min. and the CSTR was maintained at about 40° C. and a pH of about 9.0. The composition of the organic material in the CSTR output contained 80.8 molar-% BCH, 13.0 molar-% BO, and 6.2 molar-% byproducts.

EXAMPLE 2

A 31° C. aqueous stream containing 1.40 wt % caustic was pumped at 161 g/min. into the continuous tubular reactor and $Cl_2$ was added at a rate of 3.2 g/min. The resulting chlorinating species containing solution was then added to the CSTR. The butylene was added to the CSTR at a rate of 2.8 g/min. and the CSTR was maintained at about 40° C. and a pH of about 9.5. The composition of the organic material in the CSTR output contained 54.9 molar-% BCH, 38.9 molar-% BO, and 6.2 molar-% byproducts.

EXAMPLE 3

A 28° C. aqueous stream containing 1.12 wt % caustic was pumped at 145 g/min. into the continuous tubular reactor and $Cl_2$ was added at a rate of 2.8 g/min. The resulting chlorinating species containing solution was then added to the CSTR. The butylene was added to the CSTR at a rate of 2.2 g/min. and the CSTR was maintained at about 52° C. and a pH of about 7.5. The composition of the organic material in the CSTR output contained 86.1 molar-% BCH, 3.7 molar-% BO, and 10.2 molar-% byproducts.

EXAMPLE 4

A 27° C. aqueous stream containing 1.10 wt % caustic was pumped at 178 g/min. into the continuous tubular reactor and $Cl_2$ was added at a rate of 3.0 g/min. The resulting chlorinating species containing solution was then added to the CSTR. The butylene was added to the CSTR at a rate of 2.7 g/min. and the CSTR was maintained at about 52° C. and a pH of about 8.2. The composition of the organic material in the CSTR output contained 80.5 molar-% BCH, 11.5 molar-% BO, and 8.0 molar-% byproducts.

EXAMPLE 5

A 40° C. aqueous stream containing 0.93 wt % caustic was pumped at 298 g/min. into the continuous tubular reactor and $Cl_2$ was added at a rate of 5.0 g/min. The resulting chlorinating species containing solution was then added to the CSTR. The butylene was added to the CSTR at a rate of 4.0 g/min. and the CSTR was maintained at about 74° C. and a pH of about 6.5. The composition of the organic material in the CSTR output contained 88.0 molar-% BCH, 0.0 molar-% BO, and 12.0 molar-% byproducts.

EXAMPLE 6

A 60° C. aqueous stream containing 1.6 wt % caustic was pumped at 67 g/min. into a continuous tubular reactor and $Cl_2$ (99.97% pure) was added at a rate of 1.8 g/min. The resulting chlorinating species containing solution was then passed through a glass static mixer (0.95 cm diameter, 5.1 cm length) and into a water-jacketed glass CSTR. The CSTR contained four Teflon baffles and two glass, 6-bladed, flat turbine impellers positioned one above the other on an agitator shaft. Propylene (99.0% pure) was added to the CSTR below the bottom impeller through a glass-fritted sparger (10–50 micrometer pore size) at a rate of 1.1 g/min. The CSTR temperature was maintained at 60° C., ambient pressure, and a pH of about 7.3. The composition of the organic material in the CSTR output contained 91.3 molar-% propylene chlorohydrin (PCH), 4.1 molar-% propylene oxide (PO), and 4.6 molar-% byproducts. Essentially complete conversion of the chlorinating species occurred in all of the examples.

In Examples 7–9 the chlorine source was $Cl_2$ gas (99.5% pure), and it was supplied to a stirred batch reactor and contacted with a pH adjusting source until a pH of between about 10 and 11 was obtained forming a product solution containing a hypochlorite chlorinating species. The product solution containing the hypochlorite chlorinating species was then continuously fed to a 30 liter, titanium (Grade II) CSTR having titanium baffles and agitator with twin, 4-bladed, flat turbine impellers positioned one above the other on an agitator shaft. Additional $Cl_2$ was then added to the product solution in order to maintain a pH in the CSTR below at least 10.0. Olefin was supplied to the CSTR via twelve 1/32-inch (793.7 micrometer) holes located in a 4-inch (10.16 cm) diameter sparger ring constructed of 1/4-inch (6.35 mm) diameter metal tubing. The sparger ring was located below the bottom impeller and the olefin was sparged into the CSTR at a rate sufficient to maintain a slight molar excess. After the CSTR had achieved steady-state in each of the examples, organic material in the CSTR output was analyzed by gas chromatography. Essentially complete conversion of the chlorinating species occurred in all of the examples.

EXAMPLE 7

An aqueous stream containing 1.0 wt % sodium hypochlorite (NaOCl) was formed as described above using a molar ratio of $Cl_2$ to NaOH of 0.97, a reaction temperature of 20° C., and ambient pressure. The aqueous stream was fed at ambient temperature and 1340 g/min. into the CSTR and $Cl_2$ gas was co-fed at 10.0 g/min. Butylene was added to the CSTR at a rate of 18.8 g/min. The CSTR was maintained at a temperature of 33° C., a pH of about 7.6, and a pressure of 30 psig (308 kPa). The composition of the organic material in the CSTR output contained 91.1 molar-% BCH, 1.3 molar-% BO, and 7.6 molar-% byproducts.

EXAMPLE 8

An aqueous stream containing 1.5 wt % sodium hypochlorite (NaOCl) was formed as described above using a molar ratio of $Cl_2$ to NaOH of 0.97, a reaction temperature of 20° C., and ambient pressure. The aqueous stream was fed at ambient temperature and 1331 g/min. into the CSTR and $Cl_2$ gas was co-fed at 17.3 g/min. Propylene was added to the CSTR at a rate of 21.2 g/min. The CSTR was maintained at a temperature of 59° C., a pH of about 8.5, and a pressure of 60 psig (515 kPa). The composition of the organic material in the CSTR output contained 89.9 molar-% PCH, 5.7 molar-% PO, and 4.4 molar-% byproducts.

EXAMPLE 9

An aqueous stream containing 1.0 wt % calcium hypochlorite ($Ca(OCl)_2$) was formed as described above using a molar ratio of $Cl_2$ to calcium hydroxide ($Ca(OH)_2$) of 1.95, a reaction temperature of 20° C., and ambient pressure. The aqueous stream was fed at ambient temperature and 2099 g/min. into the CSTR and $Cl_2$ gas was co-fed at 20.9 g/min. Propylene was added to the CSTR at a rate of 26.9 g/min. The CSTR was maintained at a temperature of 50° C., a pH of about 7.8, and a pressure of 40 psig (377 kPa). The composition of the organic material in the CSTR output contained 93.7 molar-% PCH, 1.8 molar-% PO, and 4.5 molar-% byproducts.

Examples 1–9 indicate limited byproduct formation and high yields of desirable products. In contrast, operating outside the scope of this invention generally results in higher levels of byproduct formation and reduced product yields.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A process for preparing a chlorohydrin comprising:
   (a) contacting a chlorine source with an aqueous pH adjusting source under conditions sufficient to form a chlorinating species, said chlorinating species comprising at least one compound selected from hypochlorous acid, alkali metal hypochlorites, and alkaline earth metal hypochlorites; and
   (b) contacting, under conditions sufficient to form the chlorohydrin, the chlorinating species with at least one unsaturated organic compound that contains from 2 to 10 carbon atoms and is selected from the group consisting of substituted and unsubstituted olefins, the substituted olefins having substituents selected from the group consisting of an alkyl radical, a phenyl radical, and an alkylphenyl radical, each radical being independently either unsubstituted or substituted;
   wherein the aqueous pH adjusting source is sufficient to maintain a pH of greater than 7.0 and less than 10.0 throughout Step (b).

2. The process of claim 1 wherein the chlorine source is at least one compound selected from the group consisting of chlorine, chlorine monoxide, hypochlorous acid, alkali metal hypochlorites, and alkaline earth metal hypochlorites.

3. The process of claim 1 wherein the aqueous pH adjusting source is an aqueous mixture containing at least one type of ion selected from the group consisting of hydroxide, oxide, hypohalite, bicarbonate, and carbonate.

4. The process of claim 3 wherein the aqueous mixture is a solution of at least one type of metal ion selected from the group consisting of alkaline earth metals and alkali metals.

5. The process of claim 1 wherein the aqueous pH adjusting source is present in a concentration of from 0.1 N to 1.5 N in water.

6. The process of claim 1 wherein the organic compound is selected from the group consisting of ethylene, propylene, butulene, allyl alcohol, allyl chloride, 1-hexene, cyclohexene, and styrene.

7. The process of claim 1 wherein the organic compound is selected from the group consisting of propylene and butylene.

8. The process of claim 1 wherein the organic compound is supplied in an amount sufficient to provide a molar ratio of organic compound to chlorinating species of greater than 0.8.

* * * * *